(12) United States Patent
Farag

(10) Patent No.: US 10,357,388 B2
(45) Date of Patent: Jul. 23, 2019

(54) PROSTHESIS DELIVERY SYSTEM

(75) Inventor: Jacqueline Farag, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1079 days.

(21) Appl. No.: 13/486,588

(22) Filed: Jun. 1, 2012

(65) Prior Publication Data

US 2012/0310322 A1    Dec. 6, 2012

Related U.S. Application Data

(60) Provisional application No. 61/493,083, filed on Jun. 3, 2011.

(51) Int. Cl.
*A61F 2/966* (2013.01)
*A61F 2/07* (2013.01)
*A61F 2/95* (2013.01)

(52) U.S. Cl.
CPC .......... *A61F 2/966* (2013.01); *A61F 2/07* (2013.01); *A61F 2002/9505* (2013.01); *A61F 2002/9665* (2013.01); *A61F 2250/0039* (2013.01); *Y10T 29/4987* (2015.01)

(58) Field of Classification Search
CPC .. A61F 2/95; A61F 2/962; A61F 2/966; A61F 2002/9505; A61F 2002/9665; A61F 2002/9583; A61F 2002/9511
USPC ......................... 623/1.11, 1.12, 1.2
See application file for complete search history.

(56) References Cited

U.S. PATENT DOCUMENTS

| 5,380,304 A | 1/1995 | Parker ........................ 604/282 |
| 5,769,830 A | 6/1998 | Parker ........................ 604/282 |
| 6,258,099 B1 * | 7/2001 | Mareiro ................ A61F 2/958 604/96.01 |
| 6,607,551 B1 | 8/2003 | Sullivan et al. |
| 6,881,209 B2 | 4/2005 | Boatman et al. ............ 604/525 |

(Continued)

FOREIGN PATENT DOCUMENTS

| EP | 1690512 A1 | 8/2006 |
| EP | 1982677 A2 | 10/2008 |

OTHER PUBLICATIONS

European Search Report for corresponding EP Application No. 12170555 dated Aug. 23, 2012, 9 pages.

(Continued)

*Primary Examiner* — Diane D Yabut
*Assistant Examiner* — Socrates L Boutsikaris
(74) *Attorney, Agent, or Firm* — Brinks Gilson & Lione

(57) ABSTRACT

A deployment system is configured to deploy a prosthesis into an internal lumen of a patient. The system can include an introducer with the loaded prosthesis. A spacing mechanism can be disposed axially along the introducer. When the prosthesis is mounted onto the introducer in a radially compressed configuration, an end of a first stent and a second stent can engage a contact point of the spacing mechanism to maintain the axial distance between the first and second stents and prevent axial compression of the prosthesis during loading and deployment. The spacing mechanism can reside within the prosthesis and be disposed outwardly away from the introducer to contact the interior surface of the prosthesis. The spacing mechanism can include a flexible longitudinal member, such as a wire or strip, or a tubular body.

16 Claims, 7 Drawing Sheets

(56) References Cited

U.S. PATENT DOCUMENTS

| | | | |
|---|---|---|---|
| 6,939,337 B2 | 9/2005 | Parker et al. | 604/528 |
| 2002/0120321 A1* | 8/2002 | Gunderson et al. | 623/1.11 |
| 2003/0114909 A1 | 6/2003 | Clerc et al. | |
| 2006/0100688 A1 | 5/2006 | Jordan et al. | |
| 2008/0077224 A1* | 3/2008 | Valencia | 623/1.11 |
| 2010/0114290 A1 | 5/2010 | Rasmussen et al. | 623/1.11 |
| 2010/0198333 A1 | 8/2010 | Macatangay et al. | 623/1.15 |
| 2010/0331956 A1* | 12/2010 | Armstrong et al. | 623/1.12 |

OTHER PUBLICATIONS

European Communication for corresponding EP Application No. 12170555 dated Nov. 17, 2014, 6 pages.

\* cited by examiner

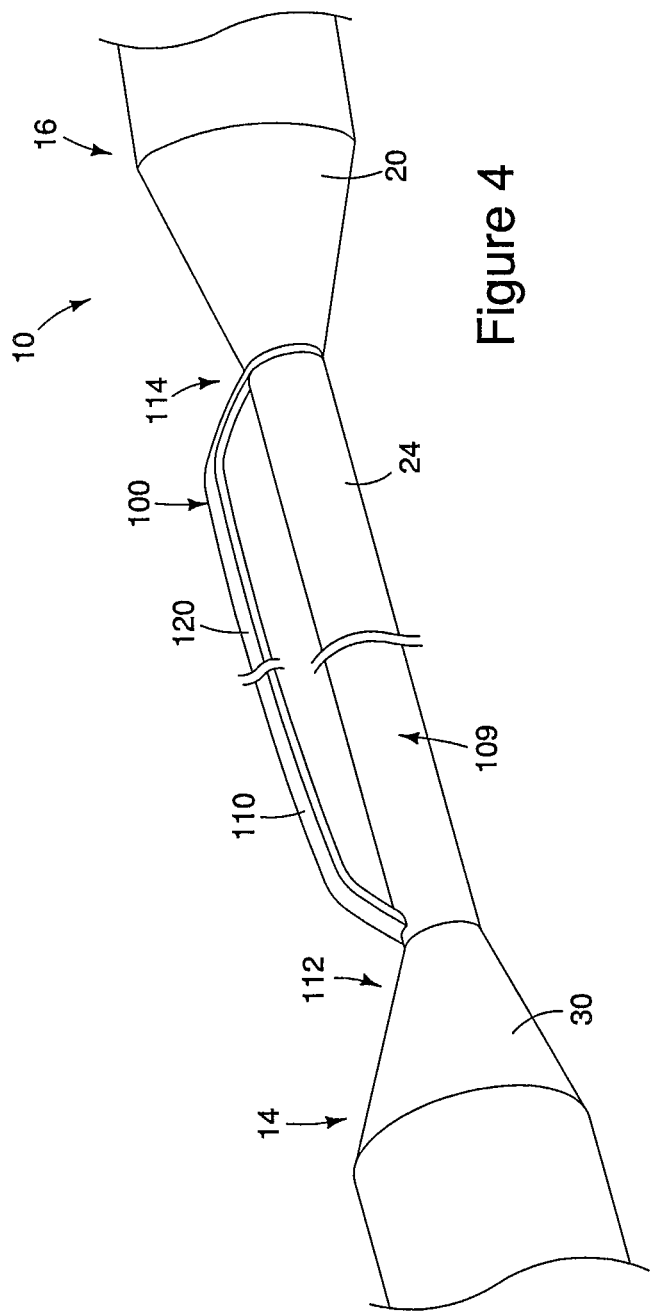
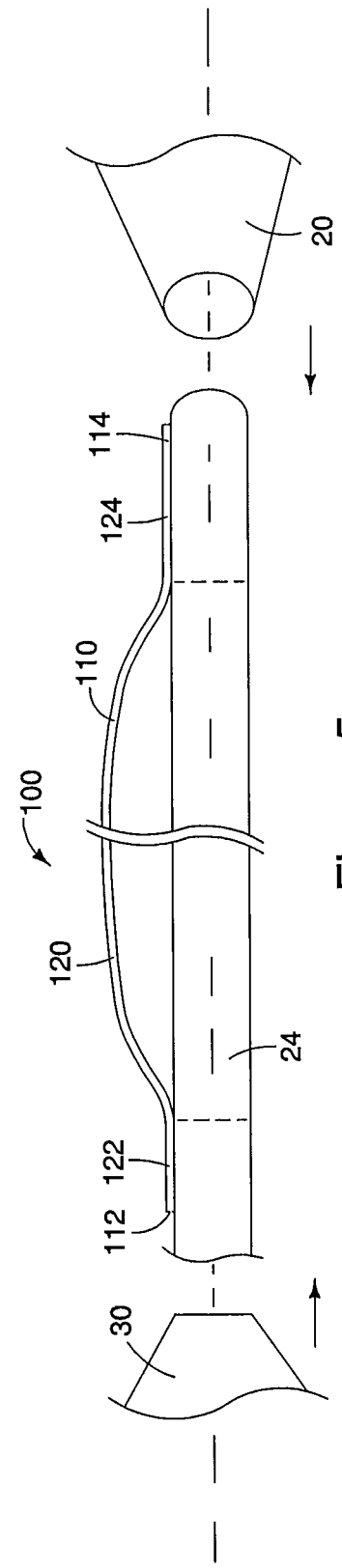

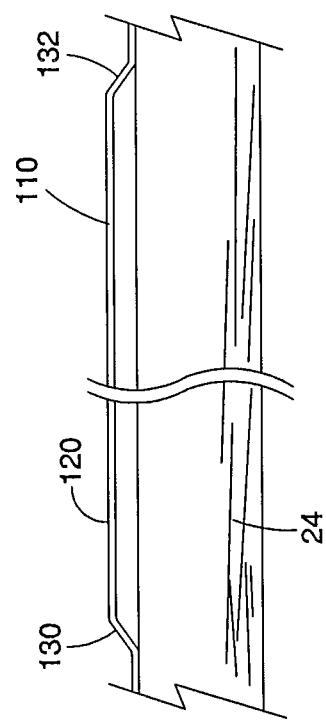
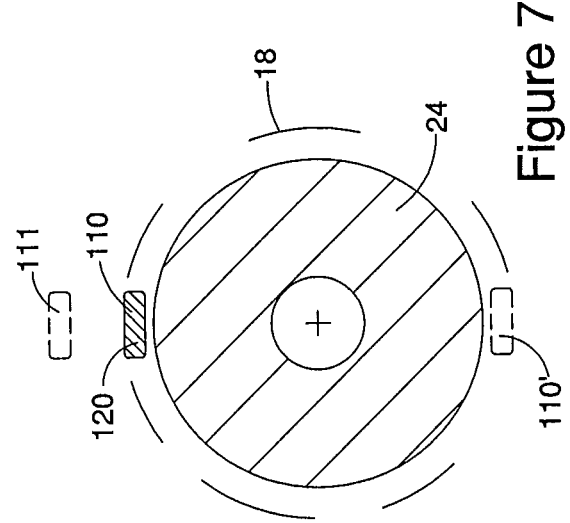

PROSTHESIS DELIVERY SYSTEM

This application claims priority to provisional application 61/493,083 filed on Jun. 3, 2011, the complete disclosure of which is incorporated herein by reference in its entirety.

TECHNICAL FIELD

The present disclosure relates to medical devices and procedures, and more particularly, to a system and method for deploying a prosthesis such as a stent graft into a bodily passageway of a patient.

BACKGROUND

Expandable endovascular prosthetic implants, such as stents and stent grafts, can be loaded into a catheter for delivery and deployment at a lesion site, such as an aneurysm or dissection within a patient's vascular system. The catheter is configured to retain the prosthetic implant in a delivery configuration during delivery to the lesion site. The catheter typically includes an inner cannula spaced from an outer sheath to define a prosthesis retaining region for receiving the prosthetic implant. The prosthetic implant is loaded onto the inner cannula along the prosthesis retaining region, with the outer sheath retaining the prosthetic implant in the delivery configuration. After the catheter is delivered to the lesion site, the prosthetic implant may be deployed with the catheter, for example, with retraction of the outer sheath relative to the inner cannula away from the prosthetic implant to allow for expansion thereof. Accurate placement of the prosthetic implant should sufficiently cover the target lesion site for endovascular treatments or procedures and the ends of the implant should be engaged with healthy tissue. Covering undesired locations with the ends of the implant, such as unhealthy vessels and/or branch vessels, due to inaccurate implant placement may cause unfavorable clinical consequences, such as branch vessel occlusion, aneurysm propagation, and/or restenosis.

Relative movement of the outer sheath during implant delivery or loading can cause axial compression and/or movement of prosthetic implant away from its desired location. The primary cause of such axial compression and/or movement is due to frictional interference or contact between the outer sheath and the prosthetic implant having a relatively low columnar strength that is expanded against the surface of the outer sheath. The frictional interference with the outer sheath can be greater than the columnar strength of the prosthetic implant, which permits deformation of the implant in the longitudinal direction, thereby collapsing the prosthetic implant in an accordion-like fashion.

Further, such axial compression and/or movement of the prosthetic implant increases the risk of a misplaced implant. That is, the misplaced prosthetic implant may not sufficiently cover the lesion site because such axial compression foreshortens the implant less than the length of the lesion site, such movement axially offsets the prosthetic implant from the lesion site, or both. For instance, axial compression of the prosthetic implant such as stent grafts with interval spacings or gaps between discrete stent segments is an increased concern to the end user. For example, during the deployment of a prosthetic implant with such interval spacing, the stent segments can converge closer to one another, also known as "bunching." Another concern is an end portion of the prosthetic implant can be moved away relative to a distal tip of the catheter, also known as "gapping."

Further, the amount of axial compression can result in stent overlap, which expands the cross-section of the implant to a degree that increases the retraction or pushing forces of the sheath necessary for deployment. In some instances, the cross-section of the implant can be sufficient to prevent any relative movement of the sheath.

In addition, loading of the prosthetic implant and the inner cannula subassembly within the outer sheath during assembly can cause such axial compression and/or movement of the prosthetic implant before deployment. Pushing or pulling the prosthetic implant and the inner cannula subassembly relative to the outer sheath typically causes axial compression or bunching of the prosthetic implant. Loading techniques with conventional catheters can result in significant axial compression of the prosthetic implant of up to 20% of the actual length of the implant. For example, for a prosthetic implant such as a stent graft having a nominal length of about 144 mm, the amount of axial compression from loading can be about 15-25 mm. With this degree of axial compression, the stent graft may be viewed under fluoroscopy to be much shorter than the nominal length, e.g., at about 119-129 mm. Consequently, the clinician may be deceived as to the actual length or loaded location of the stent graft, which may inadvertently lead to inaccurate placement of the prosthetic implant relative to the lesion site.

Thus, there remains a need to facilitate loading and/or deployment of a prosthetic implant for accurate placement of the prosthetic implant. Further, there remains a need to inhibit axial compression and/or movement of the prosthetic implant during loading and/or deployment of the prosthetic implant. The need potentially becomes more significant as the strut thickness in stents and/or the graft wall thickness become increasingly smaller to reduce the overall delivery profile of the introducer and implant.

BRIEF SUMMARY

In one embodiment, a deployment system for a stent graft to be deployed into an internal lumen of a patient is provided. The deployment system can include an introducer having a stent graft retention region at a distal end of the introducer. A stent graft can be retained along the stent graft retention region. The introducer can include an axial spacing mechanism that is disposed axially along at least a portion of the stent graft retention region. The axial spacing mechanism can have at least one of a first stent contact point and a second stent contact point. The stent contact point can extend radially from the stent graft retention region at different axial locations. The stent graft can include a tubular graft body with a lumen therethrough. A first stent and a second stent can be coupled to the graft body, each having a proximal end and a distal end. The first and second stents can be spaced from one another by an axial distance between the distal end of the first stent and the proximal end of the second stent. When the stent graft is mounted on the stent graft retention region in a radially compressed configuration, the distal end of the first stent is engageable with the first stent contact point and the proximal end of the second stent is engageable with the second stent contact point. The axial spacing mechanism can maintain the axial distance between the first and second stents at a substantially fixed distance to prevent movement such as axial compression of the stent graft during loading and/or deployment of the stent graft.

In one example of the stent graft, the first and second stents are coupled to an inside surface of the graft body, and at least one third stent is coupled to an outside surface of the graft body in between the first and second stents.

In one example of the axial spacing mechanism, an engaging intermediate portion can exert a radial outward force against an inside surface of the graft body of the stent graft in the compressed configuration. The axial spacing mechanism may be a flexible longitudinal member, such as a wire member of a metal or plastic strip, or a tubular body having a first end and a second end that are secured in a fixed position relative to the stent graft retention region of the introducer.

In another embodiment of the deployment system, a prosthesis can include a tubular graft having a first graft end, a second graft end, and an interior surface defining a graft lumen between the first and second graft ends. A first stent can be coupled to the graft proximate the first graft end, and a second stent can be coupled to the graft proximate the second graft end. At least one third stent can be coupled to the graft between the first and second graft ends. The prosthesis is radially movable between a compressed configuration and an expanded configuration. An introducer can have a prosthesis retention region at a distal end thereof, which is configured to carry the prosthesis in the compressed configuration. A spacing mechanism can be disposed axially along at least a portion of the prosthesis retention region of the introducer. The spacing mechanism can reside within the graft and be disposed outwardly away from the introducer to contact the interior surface of the graft of the prosthesis in the compressed configuration.

In another embodiment, a method of manufacturing a prosthesis delivery system is provided. The method may include attaching a first end and a second end of a spacing mechanism to an elongate member of an introducer. An engaging portion that is disposed between the first and second ends of the spacing mechanism can extend outwardly away from the elongate member. A prosthesis in a compressed configuration is positioned over the elongate member and the spacing mechanism. The prosthesis includes a graft and a first stent and a second stent spaced from one another, and coupled to the graft. The engaging portion can reside within the prosthesis and the spacing mechanism to form at least one stent contact point to contact an end of one of the first and second stents in order to retain a position of the stent relative to the elongate member. A pushing member can be positioned over the first end of the spacing mechanism and the elongate member prior to the positioning step. An axial position of the pushing member can be adjusted relative to an end of the elongate member to be in close proximity with an end of the prosthesis.

BRIEF DESCRIPTION OF THE DRAWINGS

FIG. 4 is a perspective view of a distal region of an implant deployment device provided with an example of an axial spacing mechanism in a free configuration.

FIG. 5 is a side view of a distal region of an implant deployment device illustrating an assembly of the axial spacing mechanism of FIG. 4.

FIG. 7 is a transverse sectional view of a distal region of the implant deployment device with an implant placed over the axial spacing mechanism of FIG. 4, prior to the positioning of a sheath.

FIG. 9 is a side view of a distal region of an implant deployment device of the axial spacing mechanism of FIG. 4 in an engaged configuration, with the implant and the sheath removed.

DETAILED DESCRIPTION OF THE DRAWINGS AND THE PRESENTLY PREFERRED EMBODIMENTS

Figure 1:
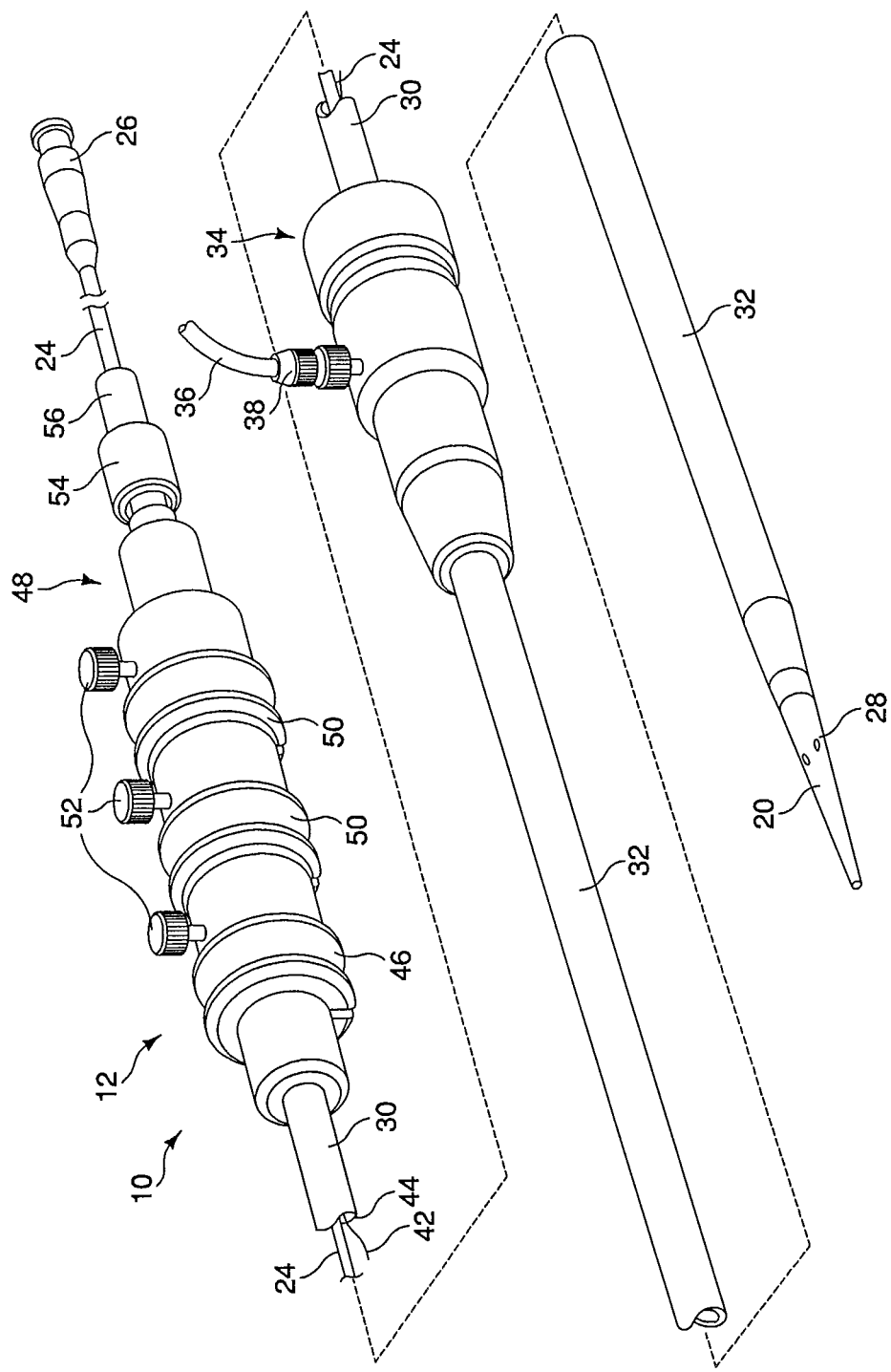
FIGS. 1 and 2 are perspective views of examples of an implant deployment device.

For the purposes of promoting an understanding of the principles of the present disclosure, reference will now be made to the embodiments illustrated in the drawings, and specific language will be used to describe the same. It is to be understood that the Figures are schematic and do not show the various components in their actual scale. In many instances, the Figures show scaled up components to assist the reader. Moreover, in the figures, like-referenced numerals designate corresponding parts throughout the different views.

In this description, when referring to a deployment assembly, the term distal is used to refer to an end of a component which in use is farthest from the surgeon during the medical procedure, including within a patient. The term proximal is used to refer to an end of a component closest to the surgeon and in practice in or adjacent an external manipulation part of the deployment or treatment apparatus.

Figure 2:
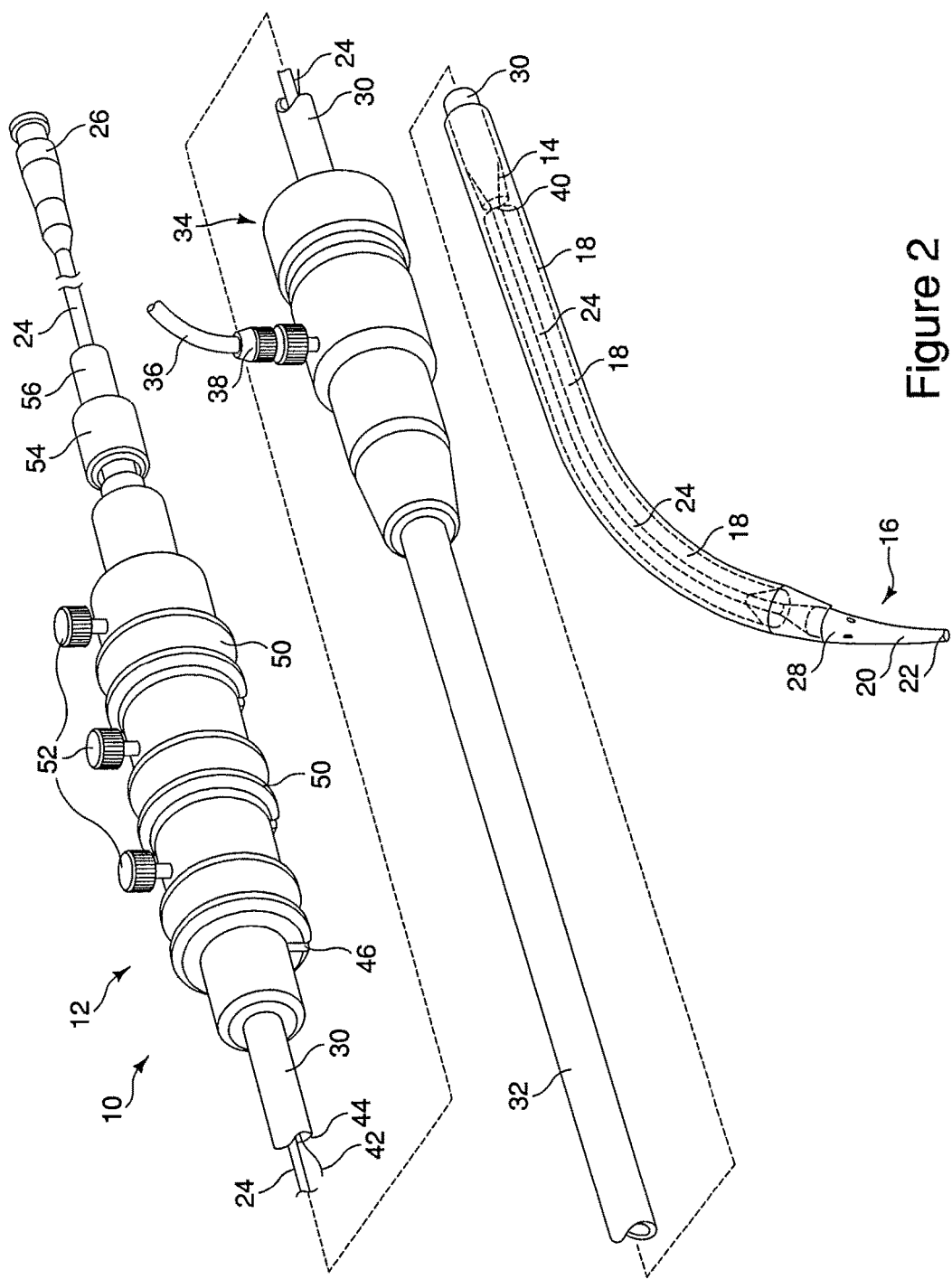

In FIGS. 1 and 2, an implant deployment device 10 can include an external manipulation section 12, a proximal attachment region 14, and a distal attachment region 16. The proximal attachment region 14 and the distal attachment region 16 may secure the two ends of the implant 18. To deploy the implant 18 during a medical procedure, the proximal and distal attachment regions 14, 16 will travel through the patient's vasculature, in this example, to a desired deployment site. The external manipulation section 12 located at the proximal end of the implant deployment device 10, which can be operated by a surgeon to manipulate the deployment device, can remain outside of the patient throughout the procedure.

The distal attachment region 16 of the implant deployment device 10 can include a dilator tip 20, which may be provided with a bore 22 longitudinally formed therein for receiving a guide wire (not shown) of a conventional type. The longitudinal bore 22 may provide a channel for the introduction of medical reagents. For example, it may be desirable to supply a contrast agent for angiography to be performed during placement and deployment phases of the medical procedure.

An inner catheter or cannula 24 can be fastened to the dilator tip 20. The inner catheter 24 can be made from a thin walled metal tube. The inner catheter 24 can be flexible so that the implant deployment device 10 can be advanced along a relatively tortuous vessel, such as a femoral artery, and so that the distal end of the implant deployment device 10 can be longitudinally and rotationally manipulated. The inner catheter 24 can carry the implant 18 to be implanted in the patient. The inner catheter 24 can be extended through the implant deployment device 10 to the external manipulation section 12, terminating at a connection device 26, in conventional manner. The connection device 26 can be configured to accept a syringe to facilitate the introduction of reagents into the inner catheter 24 and for this purpose is typically provided with a threaded luer lock connection. The inner catheter 24 can be in fluid communication with apertures 28 in the dilator tip 20. Therefore, reagents introduced into connection device 26 can flow to and emanate from the apertures 28.

Where provided, a pusher sheath or rod 30 (hereinafter referred to as a pusher member) can be mounted coaxial with and radially outside of the inner catheter 24. The pusher member 30 can be made from a plastics material. In one example, the pusher member 30 is "thick walled," that is, the thickness of its wall is preferably several times greater than that of the inner catheter 24. In some instances, the pusher member 30 and the inner catheter 24 are the same component, possibly having different outer diameters at the location at which the implant 18 is to be carried.

A sheath 32 can be provided to extend coaxially over and radially outside of the pusher member 30. The pusher member 30 and the sheath 32 can extend distally to the external manipulation region 12. The implant 18 can be retained in a compressed configuration by the sheath 32. The sheath 32 can extend proximally to a sheath manipulator and haemostatic sealing unit 34 of the external manipulation section 12. The haemostatic sealing unit 34 may include a haemostatic seal (not shown) and a side tube 36 coupled to the unit 34 by a conventional luer lock 38. The sheath manipulator and haemostatic sealing unit 34 can also include a clamping collar (not shown) that clamps the sheath 32 to the haemostatic seal and a silicone seal ring (not shown) that forms a haemostatic seal around the pusher member 30. The side tube 38 can facilitate the introduction of medical fluids, such as saline solution, in an annular space 44 between the pusher member 30 and the sheath 32.

During assembly of the implant deployment device 10, the sheath 32 can be advanced over the proximal end of the dilator tip 20 of the proximal attachment region 16 while the implant 18 is held in the compressed configuration by an external force. Proximal and distal attachment sections to maintain the implant in the compressed configuration and to control the expansion of each end of the implant may be provided with the device 10. A suitable distal attachment (retention) section (not visible in this view) may be coupled to the pusher member 30 and may retain a first, proximal end 40 of the implant 18 during the medical procedure. The proximal end 40 of the implant 18 may be provided with a loop of material (not shown) through which a distal restraining wire 42 may extend. The distal restraining wire 42 may also extend through an aperture (not shown in FIGS. 1 and 2) in the proximal attachment (retention) section 14 into the annular space 44 between the inner catheter 24 and the pusher member 30. The distal restraining wire 42 can extend through the annular space 44 to the external manipulation region 12 and can exit the annular space 44 at a distal wire release mechanism 46.

A proximal portion of the external manipulation section 12 can include at least one restraining wire actuation section 50 mounted on a body 48 that is mounted onto the pusher member 30. The inner catheter 24 can pass through the body 48. The distal wire release mechanism 46 and the proximal wire release mechanism 50 can be mounted for slidable movement on the body 48. Clamping screws 52 can be provided to prevent inadvertent early release of the implant 18. A haemostatic seal (not shown) can be included so that the release wires can extend out through the body 48 without unnecessary blood loss during the medical procedure.

A proximal portion of the external manipulation section 12 can include a pin vice 54 mounted onto the proximal end of the body 48. The pin vice 54 can have a screw cap 56. When screwed in, vice jaws (not shown) of the pin vice 54 can clamp against or engage the inner catheter 24. When the vice jaws are engaged, the inner catheter 24 can only move with the body 48 and hence it can only move with the pusher member 30. With the screw cap 56 tightened, the entire assembly can be moved together as one piece.

Once the implant deployment device 10 is in the desired deployment position, the sheath 32 can be withdrawn and the proximal and distal wire release mechanisms 50, 46, when present, can be released to allow the implant 18 to move to an expanded configuration. For some procedures, the sheath 32 may be left in place after expansion of the implant 18. The pusher member 30 and inner catheter 24 may be withdrawn and replaced by a further component, using the sheath 32 as a guide component for tracking there along.

Figure 3:
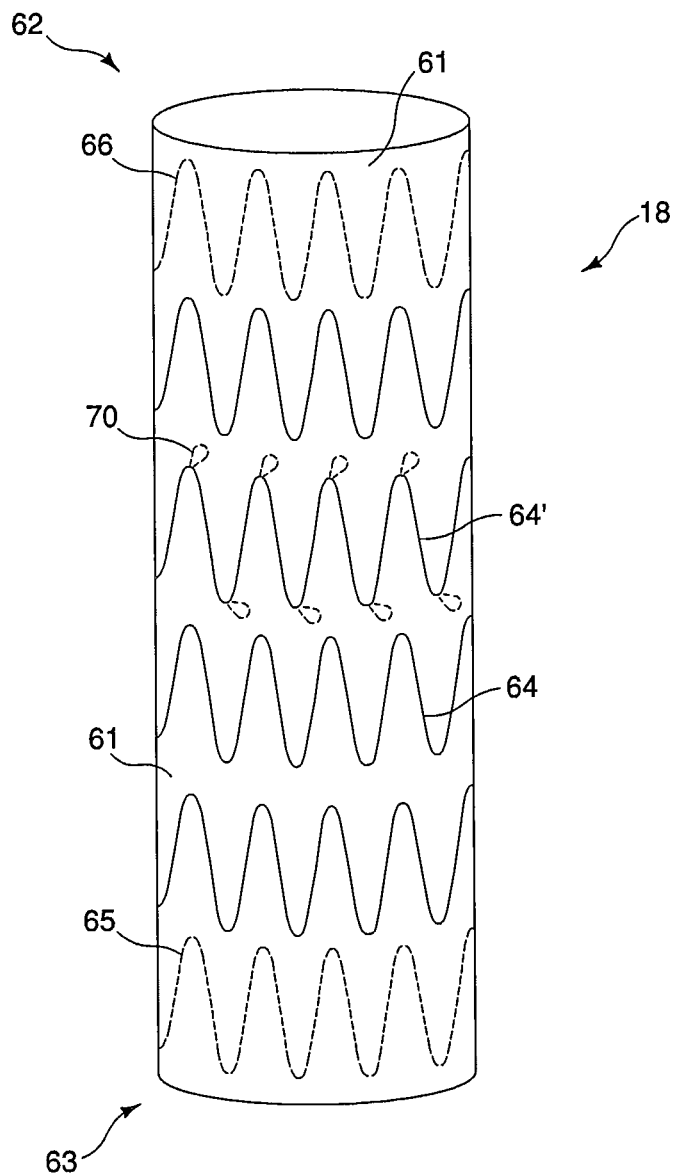
FIG. 3 is a perspective view of an implant.

FIG. 3 illustrates one example of the implant 18 for deployment within a body lumen, although the implant can be any device that is intended to be implanted into a lumen of a patient, such as, e.g., a stent, stent graft, vena cava filter, or other prosthetic device. The implant 18 can include a graft material 61 which may be substantially cylindrical tube to define a graft lumen. The graft material tube 61 can have a first, distal end 62 and a second, proximal end 63, corresponding to the proximal end 40 of the implant. The graft 61 can have a number of support structures, such as first stents 65, second stents 66, and third stents 64. The third stents 64 can be self-expanding zig-zag stents such as well-known Gianturco Z-stents, although balloon expandable stents may be used. The third stents 64 can be positioned at intervals along the length of the graft 61. In one example, the third stents 64 can be positioned along the outside surface of the graft 61. When expanded, the third stents 64 can provide the radial force sufficient to open and maintain the graft 61 out to the walls of the body lumen when deployed to allow the passage of fluid therethrough. First and second stents 65, 66 can be provided along the length of the graft at the proximal end 63 and distal end 62, respectively. The implant may have a third stent 64 provided along the exterior length of the graft in the form of spiral Z-stent that is helically coupled to the tubular graft, located between the first and second stents. One example of such implant is described in U.S. Pat. Publ. No. 2010/0198333 to Macatangay, which is incorporated herein by reference in its entirety.

In one example, the first and second stents 65, 66 can be positioned along the inside surface of the graft, while the other intermediate third stents 64 are on the outside of the graft. The first and second stents 65, 66 can be self-expanding zig-zag stents such as well-known Gianturco Z-stents, although balloon expandable stents may be used. In one example, loop members 70, such as loops of suture material, may be attached to one of the stents 64'. Loop members 70 can be equally spaced around the stent. The loop members are able to engage with a release wire, such as the distal restraining wire 42 of the implant deployment device 10. The purpose of this arrangement is described in U.S. Pat. Publ. No. 2010/0114290 to Rasmussen, which is incorporated herein by reference in its entirety. One example implant is the ZENITH® endovascular graft, which is commercially provided by Cook Medical Inc. (Bloomington, Ind.).

In FIG. 4, the implant deployment device 10 can include a spacing mechanism such as an axial spacing mechanism 100 located at the distal region of the implant deployment device 10. The axial spacing mechanism 100 can be configured to retain position of the implant 18 relative to the inner catheter 24 during loading and/or deployment of the implant. This arrangement can inhibit axial compression and/or movement of the prosthetic implant, such as bunching or gapping, during loading and/or deployment of the implant. In one example, the axial spacing mechanism 100 can maintain the axial spacing between the inner ends of the first and second stents 65, 66. It is contemplated that the axial spacing mechanism can be configured to maintain the relative position of just one of the inner ends of the first and second stents 65, 66 for similar purposes. In one example, the axial spacing mechanism 100 can include a longitudinal member 110. The longitudinal member 110 can be coupled to the inner catheter 24. A first, proximal end 112 of the longitudinal member 110 can be coupled near distal end of the pusher member 30 and a second, distal end of the longitudinal member 110 can be coupled near the proximal end of the dilator tip 20. This permits the longitudinal member 110 to extend between the pusher member 30 and the dilator tip 20 within a prosthesis retention region 109. The longitudinal member 110 may have at least a portion spaced outwardly from the surface of the inner catheter 24, as described herein.

FIG. 5 illustrates an exemplary assembly of the implant deployment device 10 with the longitudinal member 110. The proximal end 112 and the distal end 114 of the longitudinal member 110 can be secured in a fixed position relative to the inner catheter 24. The proximal and distal ends 112, 114 can be attached by various attachment mechanisms, such as welding, soldering, adhesive bonding, fusing, mechanical interference fit, or the like. When attached, the proximal and distal ends 112, 114 of the longitudinal member 110 can be separated from one another by a distance that is less than the total linear length of the longitudinal member between its ends. As a result, the longitudinal member 110 can appear to bow outwardly like an arc so that an intermediate portion 120 of longitudinal member 110 between the fixed proximal and distal ends 112, 114 is spaced outwardly away from the inner catheter 24.

It is further contemplated that the attachment of the proximal and distal ends 112, 114 of the longitudinal member 110 can be at a substantially fixed distance therebetween to accommodate a variety of implant lengths to facilitate manufacturing and assembling. To this end, the mounting location of the pusher member 30 onto the inner catheter 24 may vary relative to the fixed location of the end of the inner catheter 24, such as the distal tip 20. The attachment of the proximal and distal ends 112, 114 of the longitudinal member 110 can be attached to have a separated distance from each other suitable for the longest implant to be delivered by the device 10. In one example for an implant having a total length of about 144 mm, the proximal and distal ends 112, 114 of the longitudinal member 110, having a length of about 180 mm, can be at a separated distance from each other, such as, e.g., about 164 mm to about 174 mm. The pusher member 30 can then be located from the proximal end of the distal tip 20 by a distance of about the length of the implant, or 144 mm. For a shorter implant, such as about 61 mm, the pusher member 30 can be moved over a greater proximal length of the longitudinal member to be closer to the dilator tip 20 so that the separated distance is about the size of the shorter implant. To this end, the attachment step of the longitudinal member 110 to the inner catheter 24 in the manufacturing process can be uniform for various lengths of the implant, while the mounting location of the pusher member can be adjusted according to the size of the implant.

As shown in FIG. 5, a first end segment 122 of the longitudinal member 110 proximate the proximal end 112 can lie against the surface of the inner catheter 24. The pushing member 30, when being placed around the inner catheter 24, can then be inserted over the first end segment 122 to facilitate retaining the first end segment fixed in a secured position with respect to the inner catheter. A second end segment 124 of the longitudinal member 110 proximate the distal end 114 can lie against the surface of the inner catheter 24. The dilator tip 20, when being placed around the inner catheter 24, can then be inserted over the second end segment 124 to facilitate retaining the second end segment fixed in a secured position with respect to the inner catheter. FIG. 4 illustrates a complete assembly of the axial spacing mechanism 100 with the longitudinal member 110.

To load the implant 18 onto the implant deployment device 10 after the adjustable pusher member 30 is fixed at a desired location, a segment of the inner catheter 24 is inserted within the implant 18 that is constrained in the compressed configuration by a temporary retainer sheath (not shown). The inner catheter 24, the pusher member 30, the dilator tip 20, and the implant retained by the temporary sheath can define a subassembly. A distal end of the subassembly can be inserted within the proximal end of the sheath 32. During insertion, the temporary retainer sheath is removed from the implant so that the implant is retained in the compressed configuration by the sheath 32. After initial insertion, the subassembly is translated within the sheath 32, with the pushing member 30 pushing the implant 18 to the distal end of the sheath. The distal end of the sheath is then aligned to a desired location relative to the dilator tip 20.

Figure 6:
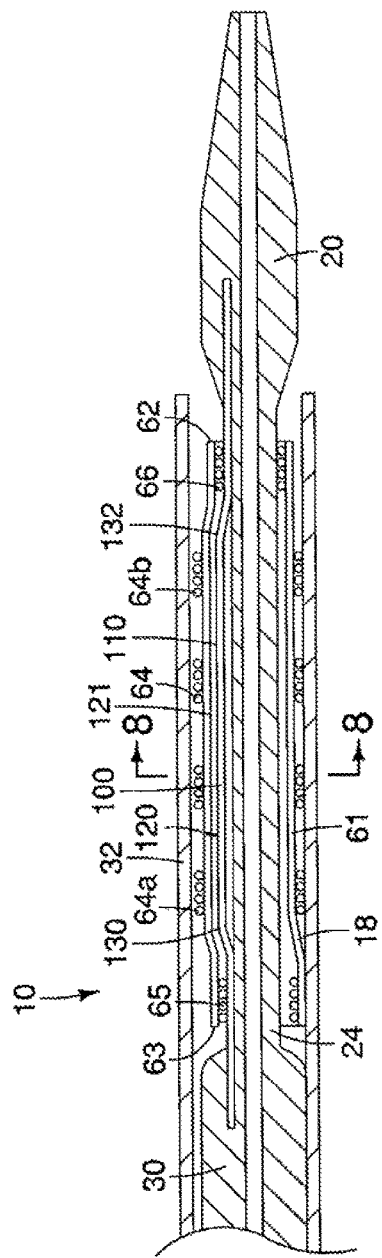
FIG. 6 is a transverse sectional view of a distal region of an implant deployment device depicting an implant loaded over the axial spacing mechanism of FIG. 4.

FIG. 6 illustrates the implant 18 in the compressed configuration placed over the longitudinal member 110 after the sheath 32 is aligned relative to the dilator tip 20. The sheath 32 is moved to a delivery configuration to extend to the distal tip 20 in order to retain the implant 18. Relative movement between the sheath 32 and the subassembly can allow for the expansion of the implant with the body lumen of a patient.

Figure 8:
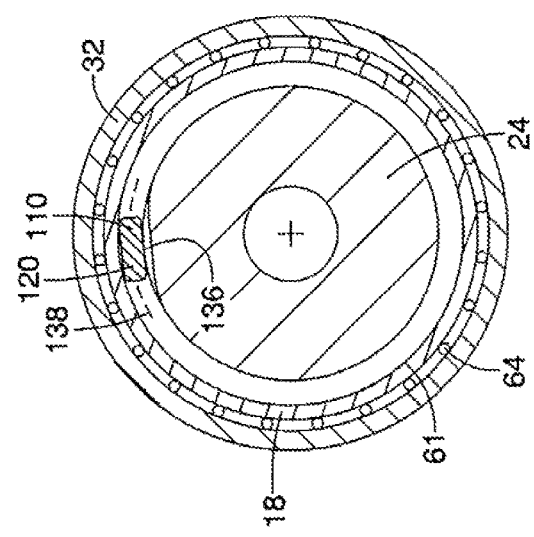
FIG. 8 is a transverse sectional view of the distal region of the implant deployment device taken along lines 8-8 of FIG. 6.

According to FIG. 7, the intermediate portion 120 of the longitudinal member 110 is shown in the free configuration, shown as reference numeral 111, extending outwardly away from the inner catheter 24. When the implant is in the compressed configuration, the intermediate portion 120 of the longitudinal member 110 may be moved closer toward the inner catheter 24 to an engaged configuration where the intermediate portion is engageable with the implant as shown in FIG. 8. In the engaged configuration, the intermediate portion 120 may extend outward from the inner catheter 24 by a gap 136, which is a smaller distance than when in the free configuration shown in FIG. 7. When in the engaged configuration, an engaging portion 121 of the longitudinal member disposed between the first and second stent contact points engage the interior surface of the implant. The outer surface of the longitudinal member which contacts the first and second stents can be spaced outwardly away from the inner catheter 24 at a distance to cover at least a portion of the struts of the stents (shown by dashed line 138). For instance, for a strut thickness of about 0.4 to about 0.45 mm, the outer surface can extend to cover for example at least 50% of the strut thickness to prevent premature slippage during loading and/or deployment. To this end, the outer surface may be extended outwardly by a total distance of about 1 mm to about 1.5 mm from the inner catheter 24.

As a result of the placement of the implant 18 over the longitudinal member 110 in the engaged configuration, a first stent contact point 130 and a second stent contact point 132 can be formed from the longitudinal member 110, as shown in FIG. 7 and FIG. 9. The stent contact points 130, 132 can be strategically located to be adjacent, if not in an abutting relationship with, the inner ends of stents, such as the first and second stents 65, 66. For instance, the stent contact points may be located a distance from the ends of the graft, e.g., about the axial length of the first and second stents, which can be about 15 mm to about 25 mm from the graft ends. The axial length of the first stent 65 can be different than the axial length of the second stent 66, such as, e.g., about 22 mm for the first stent and about 17 mm for the second stent. In one example, the first and second stents 65, 66 can overlie and can directly contact the longitudinal member.

The stent contact points 130, 132 can be formed in the interval region or gap between the first stent 65 and the adjacent third stent 64A and in the interval region between the second stent 66 and the adjacent third stent 64B. Because of the gap spacing within the interval region, the longitudinal member 110 can configured to resiliently extend away from the inner catheter 24. Since the third stents 64 are shown along the exterior surface of the graft 61, the intermediate portion 120 of the longitudinal member 110 may contact the inside surface of the graft 61 without stents underneath the region of the third stents.

To this end, the axial spacing between the inner ends, i.e., the distal end of the first stent 65 and the proximal end of the second stent 66 can be maintained at a substantially fixed distance by the stent contact points 130, 132. The position of the implant 18 relative to the inner catheter 24 can then be retained during loading and/or deployment of the implant. For example, because of the stent contact points, primarily the first stent contact point 130, axial compression of the implant 18 toward the distal tip 20 or bunching of the implant often caused by the frictional interference of the sheath 32 during relative sliding movement to the delivery configuration can be avoided. Consequently, when viewed under imaging techniques during delivery of the implant, the actual length of the implant can be observed by clinician, rather than a foreshortened length. Further, because of the stent contact points, primarily the second stent contact point 132, axial compression of the implant 18 toward the pushing member 30, bunching of the implant, or movement of the distal end 62 of the implant 18 away from the distal tip 20 often caused by the frictional interference of the sheath 32 during movement to the deployed configuration can be avoided. Consequently, when viewed under imaging techniques during delivery of the implant, the clinician can be ensured of a more predictable loaded location of the implant 18 within the implant deployment device 10, and thus accurate placement of the implant when delivered to sufficiently cover the target lesion site to avoid covering undesired locations. Further, with such a reduced risk of bunching of the implant from the stent contact points, the forces to load and/or deploy the implant can also be reduced.

The longitudinal member 110 may be of a flexible material so that the member is conformable along the inside surface of the implant 18 within the annular space defined between the inside surface of the implant 18 and the outside surface of the inner catheter 24. The longitudinal member 110 may maintain or provide additional support along the inside surface of the implant to increase the columnar strength of the implant. Examples of flexible materials include biocompatible metals or metal alloys, such as stainless steel or nitinol, or biocompatible plastic materials, such as polyamide (nylon), polyethylene, polytetrafluoroethylene (PTFE) in the form of a wire, filament, rod, strip, or the like. In one example, the longitudinal member is a flat wire made of nitinol, which can have a width less than the diameter of the inner catheter and generally be as thin as possible without easily breaking. For instance, the width of the flat wire can be, e.g., about 0.7 mm to about 1.4 mm and the thickness can be about 0.2 mm. The longitudinal member 110, such as, e.g., the engaging portion 121, may exert a radially outward force against the interior surface of the implant when in the compressed configuration. The radial force can be sufficient to counteract shear forces from the sliding sheath and provide additional resistance to longitudinal movement of the implant. The longitudinal member may be plastically deformable such that when the implant is compressed the longitudinal member assumes the internal profile created by the inner surface of the implant along the inner catheter 24. In one example, the longitudinal member can be made of an imageable material, such as radiopaque materials that can be visualized with imaging machines as appreciated by those skilled in the art.

A single longitudinal member 110 as shown in the figures may provide a smaller delivery profile for the implant deployment device 10. However, it is contemplated that two (such as a second longitudinal member 110' placed radially opposite to the longitudinal member 110, as shown in dashed lines in FIG. 7), three, four, five, six, or more longitudinal members can be provided for the axial spacing mechanism. When multiple longitudinal members are provided, it is desirable that the longitudinal members are spaced equidistantly apart from one another around the circumference of the inner catheter.

Figure 10:
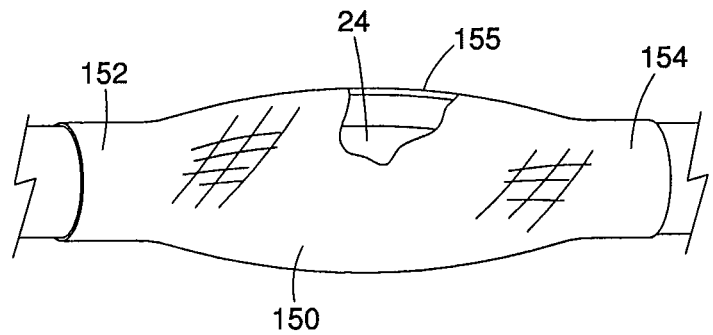
FIG. 10 shows another example of an axial spacing mechanism formed of a sleeve member.
Figure 11:
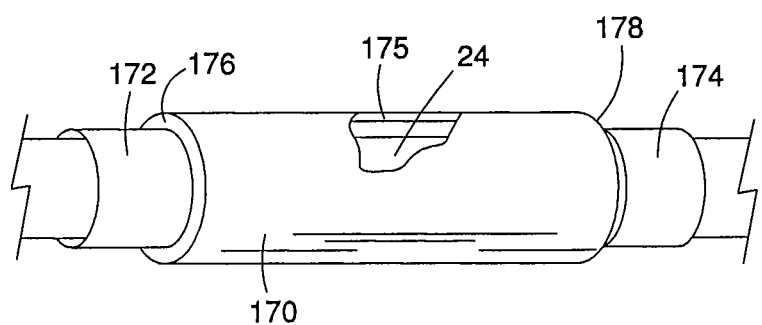
FIG. 11 shows another example of an axial spacing mechanism formed of a tubular member.

FIGS. 10-11 illustrate other examples of the spacing mechanisms comprising tubular bodies to inhibit axial compression and/or movement of the prosthetic implant during loading and/or deployment of the implant.

FIG. 10 illustrates the spacing mechanism comprising a sleeve member 150 attached to the inner catheter 24 to fit completely around the inner catheter. The first sleeve end 152 and the second sleeve end 154 can be attached to the inner catheter in a manner so that the intermediate portion 155 is placed outwardly away from the inner catheter 24. The sleeve member 150 can be a tubular member such as an extruded polymer tube or a woven or braided tube made of polymer and/or metallic filaments that are woven or braided together. Preferably, the intermediate portion 155 provides a spring force in the radially outward direction and can be biased in an outward configuration shown in FIG. 10. When a compressed implant is placed over the sleeve member 150, the sleeve member is flexible to form into the engaged configuration, similar to what is shown in FIG. 9. That is, in the engaged configuration, the first and second stent contacting points or folds can be formed adjacent to, if not in an abutting relationship with, the inner ends of the stents as described herein. The stent contacting points can maintain the axial spacing between the two stents. The intermediate portion 155 can be insertable within the interval region between two adjacent stents, preferably providing a radially outer force along the interior of the implant.

FIG. 11 illustrates the spacing mechanism comprising a tubular member 170 attached to the inner catheter 24 to fit completely around the inner catheter. A first segment 172 and a second segment 174 can be attached to the inner catheter 24 in a manner so that the intermediate portion 175 is placed outwardly away from the inner catheter 24. The intermediate portion 175 can be offset radially outward relative to the first and second segments to form an annular region between the intermediate portion and the inner catheter. The tubular member can be pre-formed to have the first and second stent contacting points 176, 178 with connecting material between the first and second segments 172, 174 and the intermediate portion 175.

The tubular member 170 can be made of unitary material and construction. However, in one example, the intermediate portion can be constructed with polymer layers, such as such as a polyether block amide, polyamide (nylon), PTFE, and/or polyurethane, and a reinforcement structure, such as a polymer and/or metal coil and/or braided polymer and/or metal filaments. Such construction of the tubular member wall is described in U.S. Pat. No. 6,939,337 to Parker et al. and U.S. Pat. No. 5,380,304 to Parker, each of which is incorporated herein by reference in its entirety.

Figure 12:
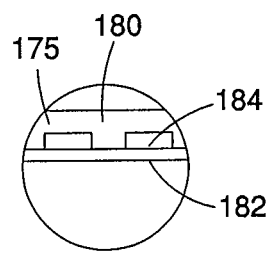
FIG. 12 is an exploded view of a wall construction of a portion of the tubular member of FIG. 11.

FIG. 12 depicts one example of an intermediate portion wall construction having an outer layer 180, an inner layer 182, and a coil structure 184. The intermediate portion can maintain a substantially cylindrical shape around the inner catheter. The first and second segment regions can be constructed with similar polymer materials so long as the first and second segments are more flexible than the intermediate portion so that the segments can lie against the inner catheter for attachment. In one example, the flexible segments may be made of a soft or lower durometer material than the intermediate portion. Lower durometer materials can include, e.g., a polyether block amide (nylon) with a durometer of approximately 25 on the Shore D scale or approximately 75 on the Shore A scale, which is described in U.S. Pat. No. 5,769,830 to Parker and U.S. Pat. No. 6,881,209 to Boatman et al., each of which is incorporated herein by reference in its entirety.

When a compressed implant is placed over the tubular member 170, the first and second stent contacting points 176, 178 can be located to be adjacent to, if not in an abutting relationship with, the inner ends of the stents as described herein. The stent contacting points can maintain the axial spacing between the two stents. The intermediate portion 175 can be insertable within the interval region between two adjacent stents, preferably providing a radially outer force along the interior of the implant.

It is contemplated that the spacing mechanism may comprise at least one strip member or a sleeve attached along a length of the inner catheter without a gap or spacing between an intermediate portion of the strip and the ends of the strip. The ends of such strip or sleeve can form the first and second stent contact points for engagement with the inner ends of the stents of the implant. The intermediate portion of such strip or sleeve can reside within the annular space between the inside surface of the implant and the inner catheter. In addition, it is contemplated that the spacing mechanism may comprise a pair of protuberances attached to the inner catheter and located specifically to form the first and second stent contact points for engagement with the inner ends of the stents of the implant. The protuberances can reside within the annular space between the inside surface of the implant and the inner catheter. Other shapes and configurations of protuberances are described in U.S. Pat. No. 6,607,551 to Sullivan et al., which is incorporated herein by reference in its entirety.

Drawings in the figures illustrating various embodiments are not necessarily to scale. Some drawings may have certain details magnified for emphasis, and any different numbers or proportions of parts should not be read as limiting, unless so-designated in the present disclosure. Those skilled in the art will appreciate that embodiments not expressly illustrated herein may be practiced within the scope of the present invention, including those features described herein for different embodiments may be combined with each other and/or with currently-known or future-developed technologies while remaining within the scope of the claims presented here. It is therefore intended that the foregoing detailed description be regarded as illustrative rather than limiting. And, it should be understood that the following claims, including all equivalents, are intended to define the spirit and scope of this invention.

The invention claimed is:

1. A deployment system for a stent graft to be deployed into an internal lumen of a patient, the deployment system comprising:
   an introducer having a stent graft retention region at a distal end of the introducer; and
   a stent graft retained along the stent graft retention region,
   the introducer comprising an axial spacing mechanism disposed axially along at least a portion of the stent graft retention region, the axial spacing mechanism having a first stent contact point and a second stent contact point extending radially from the stent graft retention region at different axial locations, wherein the axial spacing mechanism has fixed proximal and distal ends fixed to the stent graft retention region and an innermost surface of the axial spacing mechanism between the fixed proximal and distal ends is spaced radially outwardly away from the stent graft retention region and not in contact with the stent graft retention region,
   the stent graft comprising a tubular graft body having a proximal opening and a distal opening with a lumen therethrough, a first stent and a second stent coupled to the graft body, each having a proximal end and a distal end, the first and second stents being spaced from one another by an axial distance between the distal end of the first stent and the proximal end of the second stent, wherein the first stent proximal end is closer to the proximal opening than the first stent distal end is and the first stent distal end is closer to the first stent contact point than the first stent proximal end is,
   wherein when the stent graft is mounted on the stent graft retention region in a radially compressed configuration, the first and second contact points are entirely within the lumen of the stent graft and the distal end of the first stent is engaged with the first stent contact point, the proximal end of the second stent is engaged with the second stent contact point, and the axial spacing mechanism maintains the axial distance between the first and second stents at a substantially fixed distance.

2. The system of claim 1, where the first stent and the second stent are coupled to an inside surface of the graft body.

3. The system of claim 2, where the stent graft further comprises at least one third stent coupled to an outside surface of the graft body.

4. The system of claim 1, where the axial spacing mechanism further comprises an engaging portion disposed between the first and second stent contact points, the engaging portion configured to exert a radial outward force against an inside surface of the graft body of the stent graft when in the compressed configuration.

5. The system of claim 1, where the axial spacing mechanism is spaced outwardly from the stent graft retention region of the introducer by a distance to cover at least a portion of a strut thickness of the first and second stents.

6. The system of claim 1, where the axial spacing mechanism further is a flexible longitudinal member having a first end and a second end secured in a fixed position relative to the stent graft retention region of the introducer.

7. The system of claim 6, where the longitudinal member is movable between a free configuration and an engaged configuration when the stent graft in the radially compressed configuration is placed onto the longitudinal member, and in the engaged configuration the first and second stent contacts points are formed between the first and second ends of the longitudinal member.

8. The system of claim 6, where the longitudinal member is a first longitudinal member, and the system further comprises a second longitudinal member arranged radially opposite from the first longitudinal member.

9. The system of claim 1, where the axial spacing mechanism is a tubular body having a first end and a second end secured in a fixed position relative to the stent graft retention region of the introducer.

10. A delivery system comprising:
   a prosthesis including a tubular graft having a first graft end, a second graft end, an outer diameter, and an interior surface defining a graft lumen between the first and second graft ends, a first stent coupled to the graft proximate the first graft end, a second stent coupled to the graft proximate the second graft end, the prosthesis being radially movable between a compressed configuration and an expanded configuration;
   an introducer having a prosthesis retention region at a distal end of the introducer configured to carry the prosthesis in the compressed configuration; and
   a spacing mechanism disposed axially along at least a portion of the prosthesis retention region of the introducer, the spacing mechanism having a length, the spacing mechanism residing within the graft and bows radially outwardly away from the introducer at the prosthesis retention region such that the length of the spacing mechanism contacts the interior surface of the graft of the prosthesis in the compressed configuration and provides a radially outer force along the length of the interior of the graft and wherein an innermost surface of the spacing mechanism does not contact the prosthesis retention region, wherein the spacing mechanism is a flexible wire member, filament, or rod configured to prevent axial compression of the prosthesis and wherein no portion of the spacing mechanism extends beyond the outer diameter of the prosthesis.

11. The system of claim 10, where the spacing mechanism comprises at least one stent contact point extending outward from the prosthesis retention region for engagement with at least one of a distal end of the first stent and a proximal end of the second stent from within the graft, and an engaging portion to contact a region of the interior surface between the first and second stents.

12. The system of claim 11, where each of the first and second stents are coupled to the interior surface of the graft, and at least one third stent is coupled to an exterior surface of the graft.

13. The system of claim 12, where the at least one stent contact point of the spacing mechanism further comprises a first stent contact point and a second stent contact point extending outward from the prosthesis retention region for engagement with the distal end of the first stent and the proximal end of the second stent, respectively, from within the graft.

14. The system of claim 11, where the engaging portion of the spacing mechanism is configured to exert a radial outward force against a region of the interior surface of the graft without any stents.

15. The system of claim 11, where each of the first and second stent has a strut thickness, and the at least one stent contact point is displaceable outwardly by a distance sized to cover at least about 50% of the strut thickness.

16. The system of claim 10, where the spacing mechanism is a flexible wire member having a first end and a second end secured in a fixed position relative to the prosthesis retention region of the introducer so that an intermediate portion between the first and second ends extends outwardly away from the introducer.

* * * * *